(12) United States Patent
Herzog et al.

(10) Patent No.: US 12,315,871 B2
(45) Date of Patent: May 27, 2025

(54) SELF HEALING LITHIUM-ION BATTERY

(71) Applicant: STOREDOT LTD., Herzeliya (IL)

(72) Inventors: Ido Herzog, Herzeliya (IL); John Dominic Herszman, Tel Aviv-Jaffa (IL); Eran Sella, Tel Aviv (IL)

(73) Assignee: STOREDOT LTD., Herzeliya (IL)

(*) Notice: Subject to any disclaimer, the term of this patent is extended or adjusted under 35 U.S.C. 154(b) by 793 days.

(21) Appl. No.: 17/447,558

(22) Filed: Sep. 13, 2021

(65) Prior Publication Data

US 2023/0089292 A1    Mar. 23, 2023

(51) Int. Cl.
*H01M 10/0525* (2010.01)
*C07D 239/22* (2006.01)

(52) U.S. Cl.
CPC ...... *H01M 10/0525* (2013.01); *C07D 239/22* (2013.01)

(58) Field of Classification Search
CPC .................................................. H01M 4/366
See application file for complete search history.

(56) References Cited

U.S. PATENT DOCUMENTS

| | | | | |
|---|---|---|---|---|
| 9,490,045 B2* | 11/2016 | Tee | ............... | H01B 1/22 |
| 9,685,678 B2* | 6/2017 | Vu | ............... | H01M 4/587 |
| 11,087,899 B2* | 8/2021 | Wujcik | ............... | H01B 1/124 |
| 2012/0088155 A1* | 4/2012 | Yushin | ............... | H01M 4/622 |
| | | | | 977/773 |
| 2022/0173396 A1* | 6/2022 | Wang | ............... | H01M 10/0562 |

FOREIGN PATENT DOCUMENTS

| | | | | |
|---|---|---|---|---|
| CN | 111477953 B | * | 4/2021 | ...... H01M 10/0525 |
| CN | 116855022 A | * | 10/2023 | |
| EP | 4245796 A1 | * | 9/2023 | ......... C08G 61/126 |
| KR | 20210099457 A | * | 8/2021 | |
| KR | 102444310 B1 | * | 9/2022 | |
| WO | WO-2015116938 A1 | * | 8/2015 | ...... H01M 10/0525 |
| WO | WO-2020185664 A1 | * | 9/2020 | ...... H01M 10/0525 |
| WO | WO-2022056008 A1 | * | 3/2022 | ......... H01M 10/052 |

OTHER PUBLICATIONS

Lei et al, "Catalyst-free dynamic exchange of aromatic Schiff base bonds and its application to self-healing and remolding of crosslinked polymer", Journal of Materials Chemistry A Materials Horizons, 00, pp. 1-3 (2013), (Year: 2013).*

* cited by examiner

*Primary Examiner* — Amanda C. Walke
(74) *Attorney, Agent, or Firm* — Reches Patents

(57) ABSTRACT

An ion-lithium battery that may include an anode, a cathode, and at least one out of an anode related self-healing combination and a solid electrolyte interphase (SEI) self-healing combination; wherein the SEI related self-healing combination comprises a SEI self-healing additive, a SEI forming moiety and a first linker for linking the SEI self-healing additive to the SEI forming moiety; and wherein the anode related self-healing combination comprises an anode self-healing additive, an anode connection functional group, and a second linker for linking the anode self-healing additive to the anode connection functional group.

30 Claims, 6 Drawing Sheets

SELF HEALING LITHIUM-ION BATTERY

BACKGROUND

A solid electrolyte interphase (SEI) layer is formed on an anode of a lithium-ion battery during the first few charging and discharging cycles. The SEI layer provides a passivation layer on the anode surface which prevents further electrolyte decomposition and lengthens the lifespan of the lithium-ion battery.

Multiple charge and recharge cycles of a lithium-ion battery may cause the anode to shrink and expand multiple times—and these size changes may break the SEI layer—thereby exposing the anode to further electrolyte decomposition.

There is a growing need to provide a lithium-ion battery and a method for manufacturing a lithium ion battery that may heal the broken SEI layer.

SUMMARY

There may be provided a multi-electrolyte battery and a method thereof.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
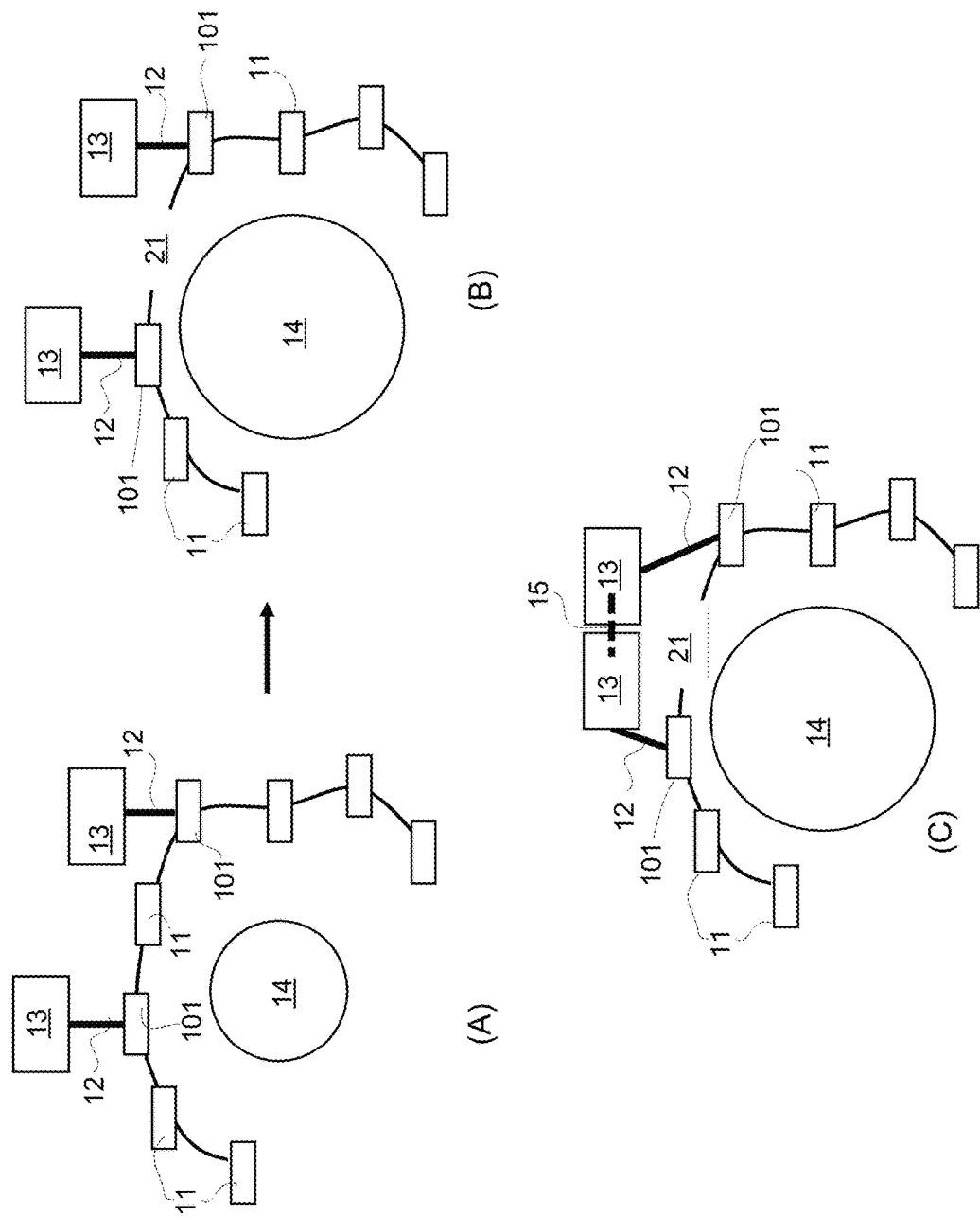
FIG. 1 illustrates examples of polymerizable self-healing (SH) additives, to induce self-healing abilities to the SEI.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a battery capable of executing the method and/or to a battery manufactured by the method.

Any reference in the specification to a battery should be applied mutatis mutandis to a method for operating the battery and/or to a method for manufacturing the battery.

Any combination of any module or unit listed in any of the figures, any part of the specification and/or any claims may be provided.

Any combination of any steps of any method illustrated in the specification and/or drawings may be provided.

Any combination of any subject matter of any of the claims may be provided.

There is provided a lithium-ion battery with self-healing functionality. The self-healing may overcome unwanted changes, such as overcoming a breaking of an SEI layer, and the like.

The lithium-ion battery may include an anode, a cathode, and at least one of an anode related self-healing combination and a solid electrolyte interphase (SEI) self-healing combination. Thus, the lithium-ion battery may include the anode related self-healing combination and the SEI self-healing combination, may include the anode related self-healing combination (and not the SEI self-healing combination), or may include the SEI self-healing combination (and not the anode related self-healing combination).

The SEI self-healing additive may prevent SEI dissolution and SEI mechanical detachment and may provide SEI reinforcement and SEI flexibility, thereby prolonging the cycle life of the lithium-ion battery.

The SEI self-healing additive may differ from the anode self-healing additive. Alternatively, the SEI self-healing additive may be equal to the anode self-healing additive.

The SEI related self-healing combination may include a SEI self-healing additive, a SEI forming moiety and a first linker for linking the SEI self-healing additive to the SEI forming moiety.

The anode related self-healing combination may include an anode self-healing additive, an anode connection functional group, and a second linker for linking the anode self-healing additive to the anode connection functional group.

The lithium-ion battery may include an electrolyte that may include the at least one out of the anode related self-healing combination and the SEI self-healing combination.

The lithium-ion battery may be manufactured by a manufacturing process that includes adding the anode related self-healing combination during a slurry preparation process.

The lithium-ion battery may be manufactured by a manufacturing process that may include adding to an electrolyte of the lithium-ion battery at least one out of the anode related self-healing combination and the SEI self-healing combination.

The lithium-ion battery may include the anode related self-healing combination and the SEI self-healing combination, wherein the SEI self-healing additive also acts as the anode self-healing additive.

The lithium-ion battery may be manufactured by a manufacturing process that may include linking the anode related self-healing combination to a part of the anode that is exposed to the electrolyte and preventing from linking the anode related self-healing combination to another part of the anode that is not exposed to the electrolyte.

The SEI related self-healing combination may be described by formula (1):

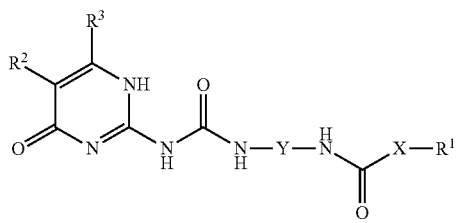

(1)

Group ($R^1$) is selected from the group of monomeric units having at least one ethylenically unsaturated group, in particular carbon-carbon triple bonds, or carbon-carbon double bonds, such as allyl alcohols, homoallyl alcohols, geraniols, pinenes, limonenes, vinylene carbonates, vinyl ethylene carbonates, propene sultones, sulfolenes, acrylates, methacrylates, acrylamides, methacrylamides, styrenes, stilbenes, vinyl-pyridines, and other vinyl monomers having a functional group selected from hydroxy, carboxylic acid, carboxylic ester, isocyanate, thioisocyanate, primary amine, secondary amine or halogen groups ([[→]]X=NH, O, S, or $CH_2$).

The linker (also referred to as linking moiety Y) may be all kinds of shorter or longer chains, for example saturated or unsaturated, branched, cyclic or linear alkyl chains, siloxane chains, ester chains, ether chains and any chain of atoms used in traditional polymer chemistry, whether or not substituted with functional groups such as esters, ethers, ureas or urethanes.

Preferably, the linking moiety (Y) is a C1-C32 linear chain or branched alkylene, arylene, alkarylene or arylalkylene group, wherein the alkylene, arylene, alkarylene or arylalkylene group may be substituted with other groups or may contain cyclic groups as substituent or in the main chain. Examples of such groups are methylene, ethylene, propylene, tetramethylene, pentamethylene, hexamethylene, heptamethylene, octamethylene, nonamethylene, isophorone; phenylene, tolylene, methylphenylene, xylylene, 4,4-biphenylenemethylene, 1,6-bis(ethylene)cyclohexane, 1,6-bis(methylene)cyclohexane, 1,6-bis(methylene)benzene, etc. The alkylene, arylene, alkarylene or arylalkylene groups may be interrupted by heteroatoms, in particular heteroatoms selected from the group of oxygen, nitrogen, and sulphur. The moiety (Y) that links the SEI-forming unit ($R^1$) to the self-healing Upy-unit is derived from a compound that must have at least two functional groups, e.g. hydroxy, carboxylate, carboxylic ester, acyl halide, isocyanate, thioisocyanate, primary amine, secondary amine, or halogen functions. These functional groups are preferably present as end groups. Such preferred compounds from which the linking moieties (Y) are derived are preferably those having isocyanate or thioisocyanate end groups.

The groups $R^2$ and $R^3$ decorating the Upy-unit may be hydrogen, methyl groups or all kinds of shorter alkyl chains.

The anode self-healing additive may be described by formula (2):

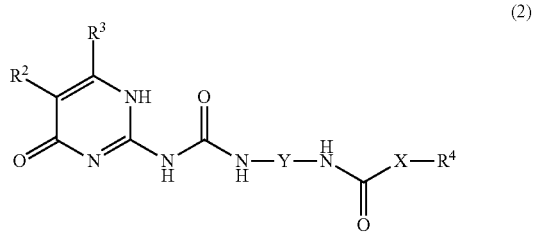

(2)

The anode connection functional group ($R^4$) is preferably chosen from the following function groups: Isocyanates, isothiocyanates, carboxylic acids or esters-COORa (with Ra=linear or branched C1-C12), alcohols, pyridines, methylpyridines, methylenepyridines, imidazoles, alkyl imidazoles, alkyl tertiary amines, or silanes having a functional group selected from hydroxy, carboxylic acid, carboxylic ester, isocyanate, thioisocyanate, primary amine, secondary amine or halogen groups ([[→]]X=NH, O, S, or $CH_2$).

Examples of the linking moiety (Y) are provided above.

FIG. 1 illustrates an example of three phases denoted (A), (B) and (C).

In (A) some SEI forming additives 11 are connected to each other to provide a barrier that prevent Si nanoparticle from further electrolyte reaction. Some of the SEI forming additives 11 are connected to the SEI forming moiety 101, which is connected via linker 12 to the self-healing unit 13. (A) also illustrates anode material 14 protected by the barrier.

In (B) a gap 21 is formed in the barrier, as a SEI forming additive 11 that was previously connected between two SEI forming moieties 101 was disconnected.

In (C) two adjacent SEI self-healing units 13 (linked by linkers 12 to two SEI forming moieties 101) are attached to each other by bond 15 to bridge a gap such as gap 21.

Figure 2:
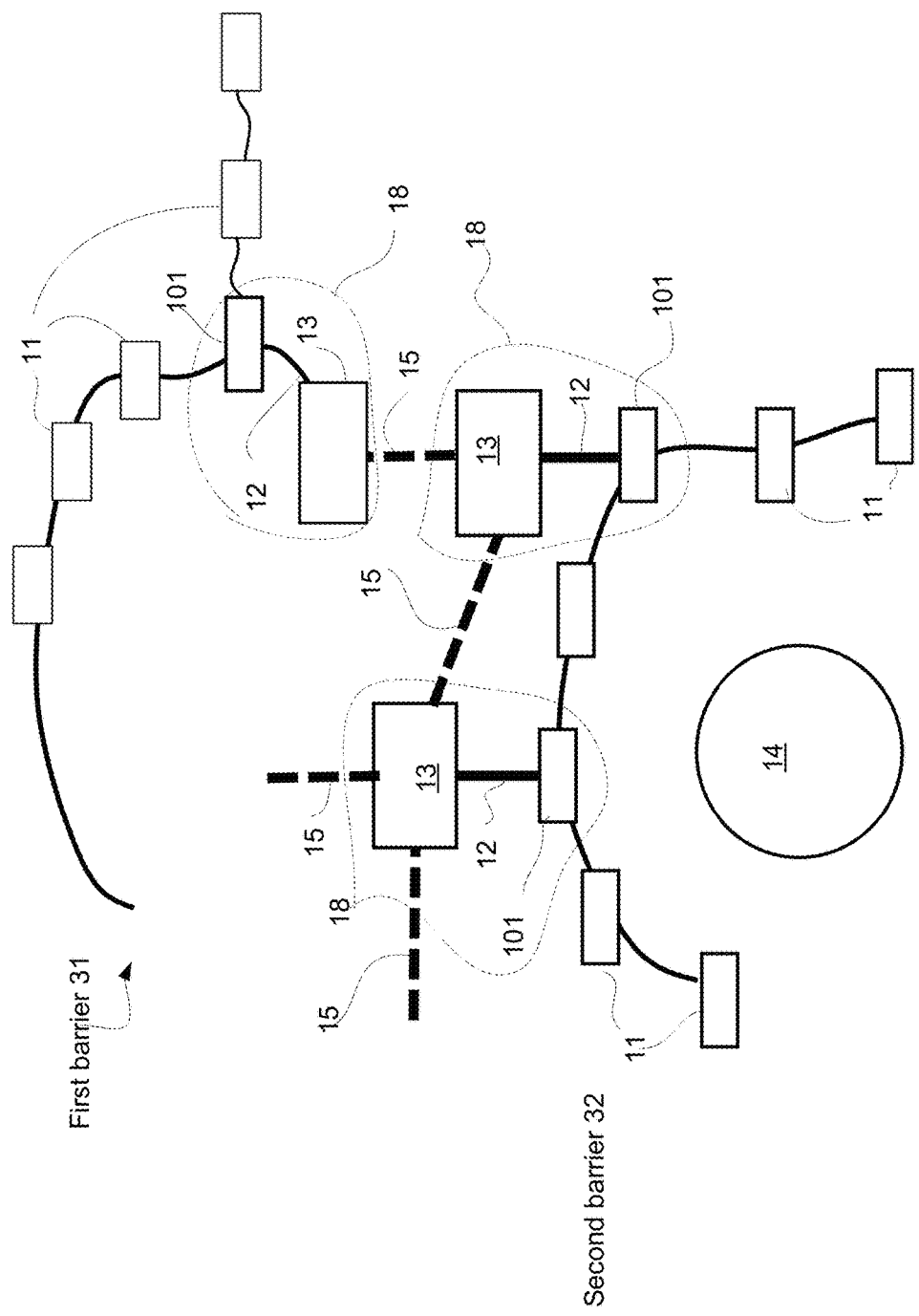
FIG. 2 illustrates examples of polymerizable self-healing (SH) additives, to induce self-healing abilities to the SEI.

FIG. 2 illustrates an example of having more than two adjacent SEI self-healing units 13 that can be attached to each other by bond 15 regardless of a formation of a gap 21. Bond 15 may be any non-covalent or covalent bond. It should be noted that self-healing moieties may contain dynamic covalent bonds (e.g. disulfides).

FIG. 2 also illustrates that some of the SEI forming additives 11 may be attached to other SEI forming additives 11 and/or to a SEI forming moiety 101.

FIG. 2 illustrates three instances of an anode SEI related self-healing combination 18—each is formed by linker 12 that is attached to SEI forming moiety 101 and SEI self-healing unit 13.

FIG. 2 illustrates a first barrier 31, a second barrier 32 and a pair of adjacent SEI self-healing units 13 connected between the first and second barriers.

Figure 3:
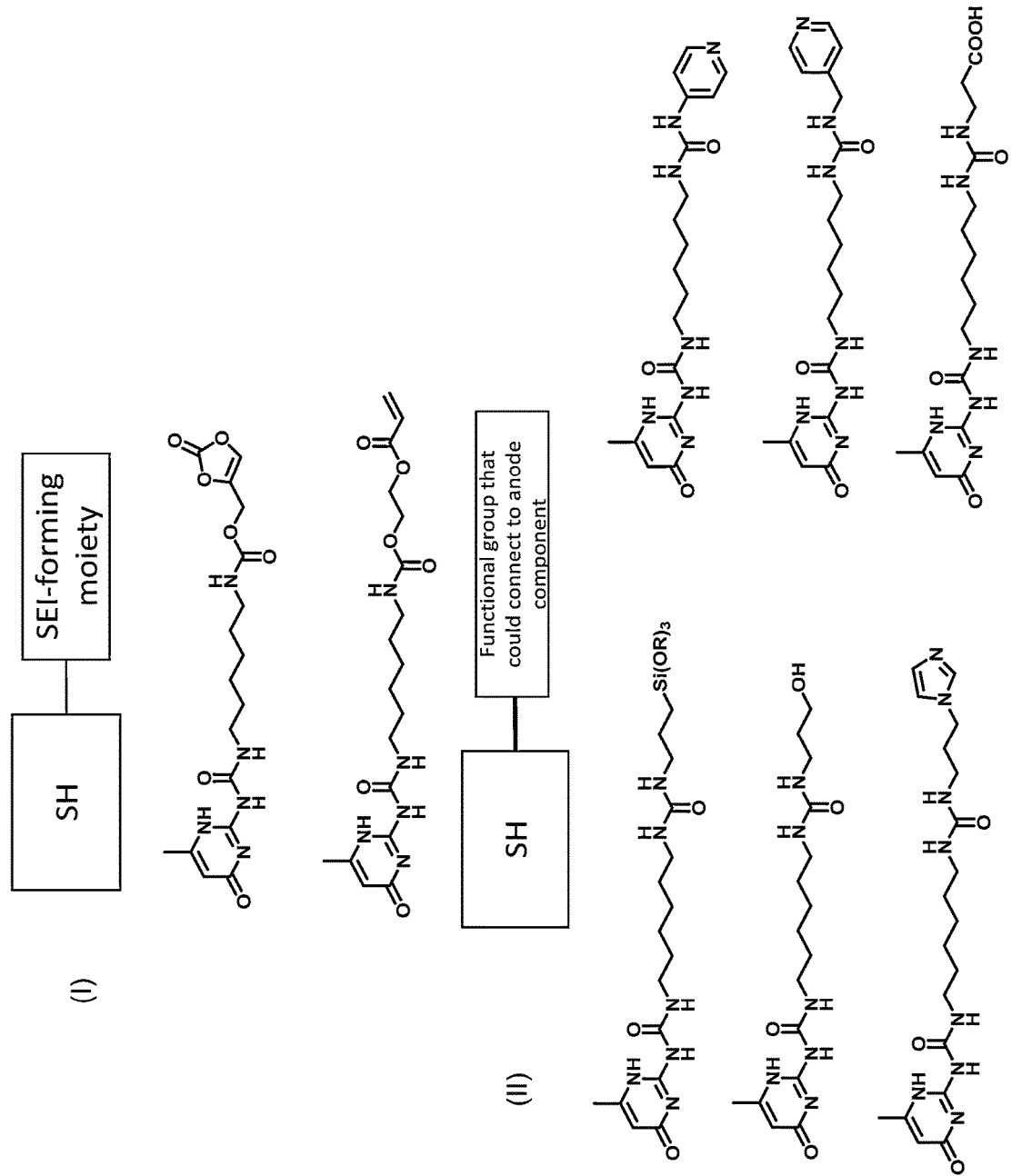
FIG. 3 illustrates examples of additives inserting self-healing (SH) function to the anode component.

FIG. 3 illustrates examples of (i) SEI self-healing additive, a SEI forming moiety and a first linker for linking the SEI self-healing additive to the SEI forming moiety, and of (ii) an anode self-healing additive, an anode connection functional group, and a second linker for linking the anode self-healing additive to the anode connection functional group. The second linker may be the same as the first linker.

Figure 4:
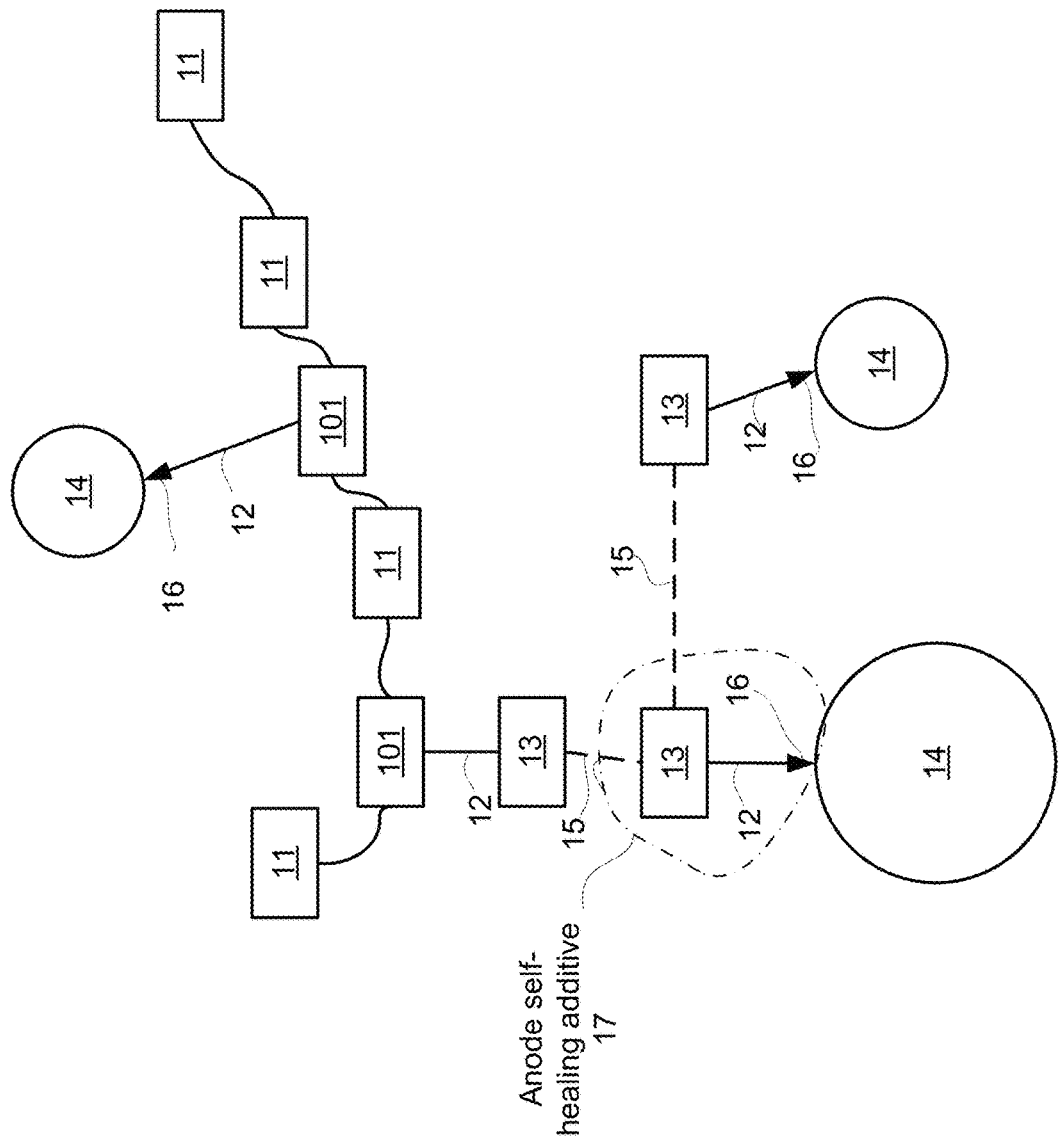
FIG. 4 illustrates examples of attaching SEI-forming additives to the anode.

FIG. 4 illustrates a self-healing anchoring idea—self-healing moiety 13 is attached to the anode material 14 by anode connection functional group 16 via linker 12. The self-healing moiety 13 can be attached via bond 15 to another self-healing moiety 13 which is either incorporated in the SEI or connected to another anode material 14. The linker 12, anode connection group 16 and the self-healing moiety 13 form an anode self-healing additive 17. FIG. 4 also illustrates a sequence that includes SEI forming moieties 101 and SEI forming additives 11. One of the SEI forming moieties 101 is attached to the anode material 14 by anode connection functional group 16 via linker 12.

Figure 5:
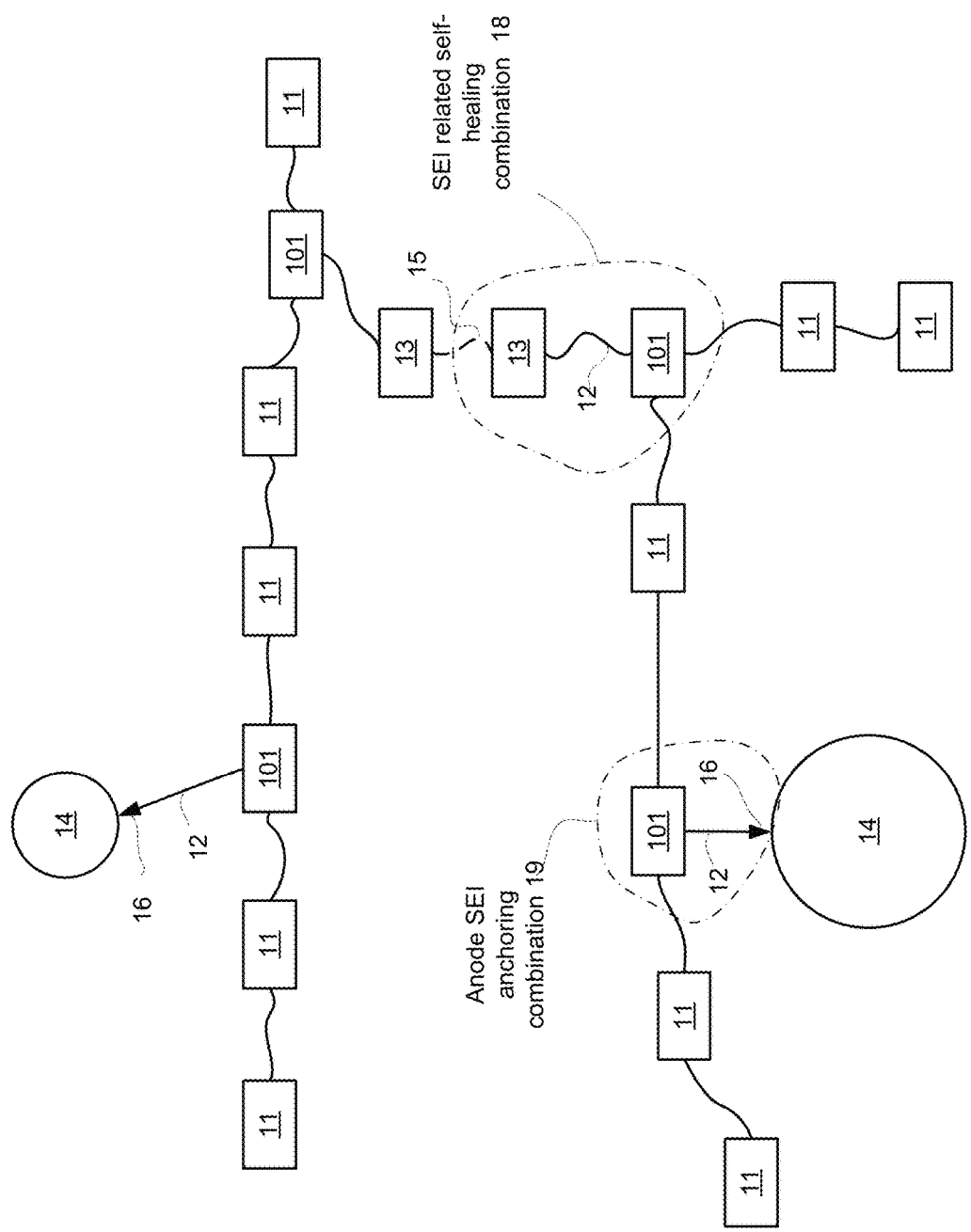
FIG. 5 illustrates examples of covalent linking.

FIG. 5 illustrates Combination of self-healing SEI with the SEI anchoring—SEI forming moiety 101 is attached to the anode material 14 by anode connection functional group 16 via linker 12. The SEI forming moiety 101 is connected to the SEI forming additives 11. This way, the formed SEI is chemically attached to the anode material.

FIG. 5 also illustrates a sequence that includes SEI forming moieties 101 and SEI forming additives 11. One of the SEI forming moieties 101 is attached to the anode material 14 by anode connection functional group 16 via linker 12. The SEI forming moieties 101, linker 12 and anode connection functional group 16 form an anode SEI anchoring combination 19. FIG. 5 also illustrated an anode SEI related self-healing combination 18 formed by linker 12 that is attached to SEI forming moiety 101 and self-healing moiety 13.

Figure 6:
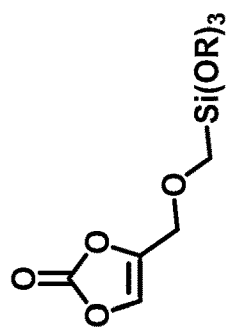
FIG. 6 illustrates examples of SEI anchoring combinations.
Figure 6:
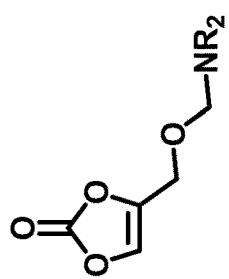
Figure 6:
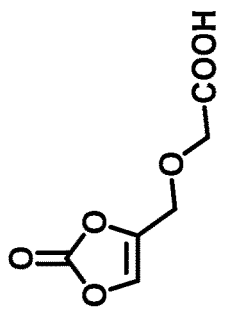
Figure 6:
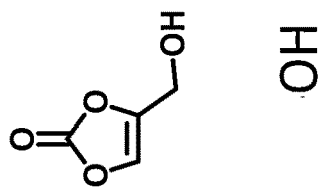

FIG. 6 illustrates examples of SEI anchoring combination 19 that follow formula (3): $R^1$—Y—$R^4$.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

In the foregoing specification, the invention has been described with reference to specific examples of embodiments of the invention. It will, however, be evident that various modifications and changes may be made therein without departing from the broader spirit and scope of the invention as set forth in the appended claims.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Any reference to "consisting", "having" and/or "including" should be applied mutatis mutandis to "consisting" and/or "consisting essentially of".

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It is appreciated that various features of the embodiments of the disclosure which are, for clarity, described in the contexts of separate embodiments may also be provided in combination in a single embodiment. Conversely, various features of the embodiments of the disclosure which are, for brevity, described in the context of a single embodiment may also be provided separately or in any suitable sub-combination.

It will be appreciated by persons skilled in the art that the embodiments of the disclosure are not limited by what has been particularly shown and described hereinabove. Rather the scope of the embodiments of the disclosure is defined by the appended claims and equivalents thereof.

We claim:

1. A lithium-ion battery with self-healing functionality, comprising:
   an anode,
   a cathode,
   at least one out of an anode related self-healing combination and a solid electrolyte interface (SEI) self-healing combination; wherein the SEI related self-healing combination comprises a SEI self-healing additive, a SEI forming moiety and a first linker for linking the SEI self-healing additive to the SEI forming moiety; and an electrolyte, wherein the electrolyte comprises the at least one out of the anode related self-healing combination and the SEI self-healing combination;

wherein the anode related self-healing combination comprises an anode self-healing additive, an anode connection functional group, and a second linker for linking the anode self-healing additive to the anode connection functional group.

2. The lithium-ion battery according to claim 1 wherein the lithium-ion battery is manufactured by a manufacturing process that comprises adding the anode related self-healing combination during a slurry preparation process.

3. The lithium-ion battery according to claim 1 wherein the lithium-ion battery is manufactured by a manufacturing process that comprises adding to an electrolyte of the lithium-ion battery at least one out of the anode related self-healing combination and the SEI self-healing combination.

4. The lithium-ion battery according to claim 1 comprising the anode related self-healing combination and the SEI self-healing combination.

5. The lithium-ion battery according to claim 4 comprising the anode related self-healing combination and the SEI self-healing combination, wherein the SEI self-healing additive also acts as the anode self-healing additive.

6. The lithium-ion battery according to claim 1 wherein the lithium-ion battery is manufactured by a manufacturing process that comprises linking the anode related self-healing combination to a part of the anode that is exposed to the electrolyte and preventing from linking the anode related self-healing combination to another part of the anode that is not exposed to the electrolyte.

7. The lithium-ion battery according to claim 1 wherein the SEI self-healing additive differs from the anode self-healing additive.

8. The lithium-ion battery according to claim 1 wherein the SEI self-healing additive equals the anode self-healing additive.

9. The lithium-ion battery according to claim 1 wherein the anode related self-healing combination is described by the formula:

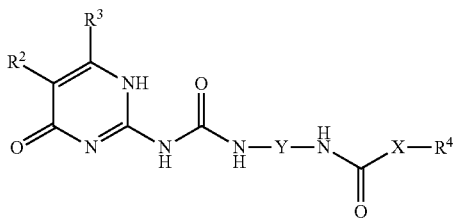

wherein $R^4$ is an anode connection functional group, wherein $R^2$ and $R^3$ are 1-4 carbon alkyl chains, X is selected from NH, O, S and CH2, and Y is a linking moiety.

10. The lithium-ion battery according to claim 9 wherein the anode connection functional group is selected out of isocyanates, isothiocyanates, carboxylic acids, alcohols, pyridines, methylpyridines, methylenepyridines, imidazoles, alkyl imidazoles, alkyl tertiary amines.

11. The lithium-ion battery according to claim 10 wherein the carboxylic esters are COORa, with Ra=linear or branched C1-C12.

12. The lithium-ion battery according to claim 10 wherein the linking moiety is selected out of saturated or unsaturated, branched, cyclic or linear alkyl chains, siloxane chains, ester chains, ether chains and any chain of atoms used in traditional polymer chemistry, whether or not substituted with functional groups such as esters, ethers, ureas or urethanes.

13. The lithium-ion battery according to claim 10 wherein the linking moiety is selected out of C1-C32 linear chain or branched alkylene, arylene, alkarylene or arylalkylene group, wherein the alkylene, arylene, alkarylene or arylalkylene group.

14. The lithium-ion battery according to claim 10 wherein the linking moiety is selected out of methylene, ethylene, propylene, tetramethylene, pentamethylene, hexamethylene heptamethylene, octamethylene, nonamethylene, isophorone; phenylene, tolylene, methylphenylene, xylylene, 4,4-biphenylenemethylene, 1,6-bis(ethylene)cyclohexane, 1,6-bis(methylene)cyclohexane, 1,6-bis(methylene)benzene.

15. The lithium-ion battery according to claim 10 wherein the linking moiety is derived from a compound that must have at least two functional groups, e.g. hydroxy, carboxylate, carboxylic ester, acyl halide, isocyanate, thioisocyanate, primary amine, secondary amine, or halogen functions.

16. The lithium-ion battery according to claim 9 wherein the anode connection functional group is selected out of silanes having a functional group selected from hydroxy, carboxylic acid, carboxylic ester, isocyanate, thioisocyanate, primary amine, secondary amine or halogen groups.

17. The lithium-ion battery according to claim 10 wherein the SEI related self-healing combination is described by the formula:

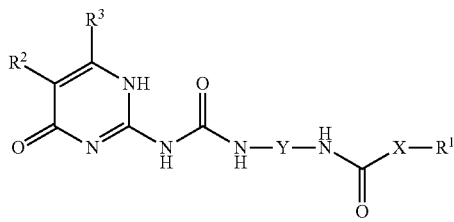

wherein $R^1$ is a SEI-forming group, wherein $R^2$ and $R^3$ are 1-4 carbon alkyl chains, X is selected from NH, O, S and CH2, and Y is a linking moiety.

18. The lithium-ion battery according to claim 17 wherein the SEI-forming/polymerizable group is selected out of monomeric units having at least one ethylenically unsaturated group.

19. The lithium-ion battery according to claim 17 wherein the SEI-forming/polymerizable group is selected out of carbon-carbon double bonds.

20. The lithium-ion battery according to claim 17 wherein the SEI-forming/polymerizable group is selected out allyl alcohols, homoallyl alcohols, geraniols, pinenes, limonenes, vinylene carbonates, vinyl ethylene carbonates, propene sultones, sulfolenes, acrylates, methacrylates, acrylamides, methacrylamides, styrenes, stilbenes, vinyl-pyridines.

21. The lithium-ion battery according to claim 17 wherein the SEI-forming/polymerizable group is selected out of vinyl monomers having a functional group selected from hydroxy, carboxylic acid, carboxylic ester, isocyanate, thioisocyanate, primary amine, secondary amine or halogen groups.

22. The lithium-ion battery according to claim 17 wherein the linking moiety is selected out of saturated or unsaturated, branched, cyclic or linear alkyl chains, siloxane chains, ester chains, ether chains and any chain of atoms used in traditional polymer chemistry, whether or not substituted with functional groups such as esters, ethers, ureas or urethanes.

23. The lithium-ion battery according to claim 17 wherein the linking moiety is selected out of C1-C32 linear chain or branched alkylene, arylene, alkarylene or arylalkylene group, wherein the alkylene, arylene, alkarylene or arylalkylene group.

24. The lithium-ion battery according to claim 17 wherein the linking moiety is selected out of methylene, ethylene, propylene, tetramethylene, pentamethylene, hexamethylene heptamethylene, octamethylene, nonamethylene, isophorone; phenylene, tolylene, methylphenylene, xylylene, 4,4-biphenylenemethylene, 1,6-bis(ethylene)cyclohexane, 1,6-bis(methylene)cyclohexane, 1,6-bis(methylene)benzene.

25. The lithium-ion battery according to claim 24 wherein the alkylene, arylene, alkarylene or arylalkylene groups are interrupted by heteroatoms, in particular heteroatoms selected from the group of oxygen, nitrogen, and sulphur.

26. The lithium-ion battery according to claim 17 wherein the linking moiety is derived from a compound that must have at least two functional groups, e.g. hydroxy, carboxylate, carboxylic ester, acyl halide, isocyanate, thioisocyanate, primary amine, secondary amine, or halogen functions.

27. The lithium-ion battery according to claim 1 comprising a SEI anchoring combination that follows formula $R^1$—Y—$R^4$, wherein Y is a linking moiety, $R^1$ is selected from the group of monomeric units having at least one ethylenically unsaturated group, in particular carbon-carbon triple bonds, or carbon-carbon double bonds, such as allyl alcohols, homoallyl alcohols, geraniols, pinenes, limonenes, vinylene carbonates, vinyl ethylene carbonates, propene sultones, sulfolenes, acrylates, methacrylates, acrylamides, methacrylamides, styrenes, stilbenes, vinyl-pyridines, and other vinyl monomers having a functional group selected from hydroxy, carboxylic acid, carboxylic ester, isocyanate, thioisocyanate, primary amine, secondary amine or halogen groups, and $R^4$ is chosen from: Isocyanates, isothiocyanates, carboxylic acids or esters —COORa, with Ra=linear or branched C1-C12, alcohols, pyridines, methylpyridines, methylenepyridines, imidazoles, alkyl imidazoles, alkyl tertiary amines, or silanes having a functional group selected from hydroxy, carboxylic acid, carboxylic ester, isocyanate, thioisocyanate, primary amine, secondary amine or halogen groups.

28. A method for manufacturing a lithium-ion battery with self-healing functionality, the method comprises: adding, during the manufacturing process, at least one out of an anode related self-healing combination and a solid electrolyte interphase (SEI) self-healing combination; wherein the SEI related self-healing combination comprises a SEI self-healing additive, a SEI forming moiety and a first linker for linking the SEI self-healing additive to the SEI forming moiety; and wherein the anode related self-healing combination comprises an anode self-healing additive, an anode connection functional group, and a second linker for linking the anode self-healing additive to the anode connection functional group; wherein the adding further comprises providing an electrolyte that comprises at least one out of the anode related self-healing combination and the SEI self-healing combination.

29. The method according to claim 28 wherein the adding comprises adding the anode related self-healing combination during a slurry preparation process.

30. A method for operating a lithium-ion battery with self-healing functionality, the method comprises:
   charging the lithium-ion battery and discharging the lithium-ion battery;
   wherein the lithium-ion battery comprises an anode, a cathode, an electrolyte, and at least one out of an anode related self-healing combination and a solid electrolyte interface (SEI) self-healing combination;
   wherein the SEI related self-healing combination comprises a SEI self-healing additive, a SEI forming moiety and a first linker for linking the SEI self-healing additive to the SEI forming moiety;
   wherein the anode related self-healing combination comprises an anode self-healing additive, an anode connection functional group, and a second linker for linking the anode self-healing additive to the anode connection functional group; wherein the electrolyte comprises the at least one out of the anode related self-healing combination and the SEI self-healing combination.

\* \* \* \* \*